United States Patent [19]

Kinsella et al.

[11] 4,427,580

[45] Jan. 24, 1984

[54] METHOD FOR SEPARATION AND RECOVERY OF PROTEINS AND NUCLEIC ACIDS FROM NUCLEOPROTEINS USING WATER DESTRUCTURING SALTS

[75] Inventors: John E. Kinsella; Damodaran Srinivasan, both of Ithaca, N.Y.

[73] Assignee: Cornell Research Foundation, Inc., Ithaca, N.Y.

[21] Appl. No.: 414,086

[22] Filed: Sep. 1, 1982

[51] Int. Cl.³ .................................................. A23J 1/18
[52] U.S. Cl. ................................. 260/112 R; 426/656
[58] Field of Search ..................................... 260/112 R

[56] References Cited

U.S. PATENT DOCUMENTS

| | | | |
|---|---|---|---|
| 3,903,314 | 9/1975 | Chao | 260/112 R X |
| 3,983,008 | 9/1976 | Shinozaki et al. | 260/112 R X |
| 3,996,104 | 12/1976 | Lindblom et al. | 260/112 R X |
| 4,210,580 | 7/1980 | Amrani | 260/112 B |
| 4,330,464 | 5/1982 | Lawford et al. | 260/112 R |

*Primary Examiner*—Howard E. Schain

[57] ABSTRACT

The present invention comprises a process for treating nucleoprotein complexes with a chaotropic salt in order to dissociate the nucleic acids from the nucleo-protein complexes, and then isoelectrically precipitating a nucleic acid diminished protein containing fraction from a nucleic acid enriched supernatant.

6 Claims, 1 Drawing Figure

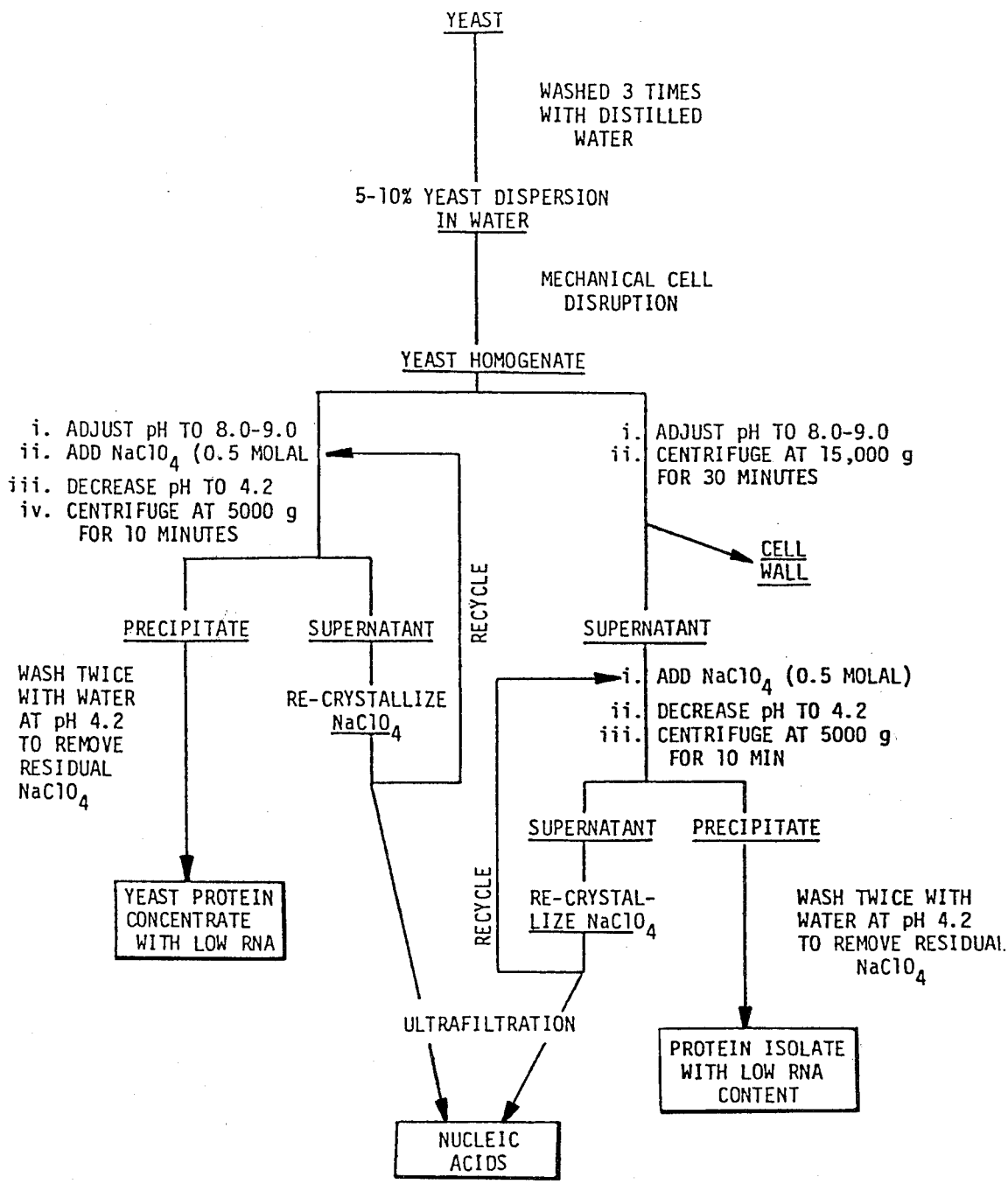

METHOD FOR SEPARATION AND RECOVERY OF PROTEINS AND NUCLEIC ACIDS FROM NUCLEOPROTEINS USING WATER DESTRUCTURING SALTS

The present invention was performed under National Science Foundation Grant No. NSF CPE80-18394.

BACKGROUND OF THE INVENTION

With an ever increasing world population there is continuing expansion in the need for high quality protein to meet human nutrient requirements. However, because of limitations in agricultural land, there will be an increasing requirement for the biosynthesis of food proteins using fermentation processes employing various microorganisms. Thus, various bacteria and yeast which can grow on inexpensive substrates can produce copious amounts of high quality proteins. This protein has great potential for use in foods. However, for the protein to be effectively used in food manufacturing and food processing it is essential that it be initially extracted and refined. One of the major problems limiting the greater use of proteins from microbes, particularly for human consumption and also for use in pet foods (particularly for monogastric animals), is the high nucleic acid content of these protein preparations. The intake of relatively high quantities of nucleic acid is undesirable because it can cause uricemia, gout and kidney stone formation. For humans, the Protein Advisory Group of the United Nations has recommended that the amount of nucleic acid ingested per day should not exceed 2 grams, and in fact, it should be much less. This means that the nucleic acid content of microbial proteins intended for food use should be less than 5% if the microbial protein supplies 50% of the dietary protein. However, proteins prepared by conventional methods from microbial sources contain from 10-27% grams/100 grams dry protein. Therefore, a practical method is needed for the reduction of the nucleic acid in proteins from microbial sources.

Furthermore, with the rapid development of recombinant DNA techniques and genetic engineering, microbes will be increasingly used for the production of materials for agricultural, biomedical and industrial uses. Thus, genetic engineering is and will be used to an increasing extent for the production of hormones; for the production of enzymes for use in biomedical and industrial applications such as in the food industry for the production of high quality proteins. However, a major difficulty in this regard is the effective separation of these proteinaceous materials from the nucleic acid materials present in the microbial cells. Because of the tremendous potential in these areas there is an urgent need for the development of a practical method for the isolation of these proteinaceous materials with a minimum of nucleic acid contamination.

In addition, the demand for nucleic acids for biomedical research (recombinant DNA) and uses in commercial products (shampoos, cosmetics) is increasing. However, the present methods for preparing large lots of these is expensive and time-consuming. The procedures described herein affords a practical method for the simultaneous separation of protein and nucleic acid for research and commercial applications.

With this background information it is obvious that a practical method, compatible with existing processing technology, which would facilitate the isolation of nucleic acids and proteinaceous material devoid of nucleic acid needs to be developed. The invention described herein provides such a method.

Several laboratory scale methods have been proposed for the reduction of nucleic acid levels in proteins isolated from microbial cells. These methods involve the chemical and enzymatic treatments of the protein-nucleic acid complex to degrade the nucleic acids and to facilitate their separation based on electrostatic charge repulsion. However, these methods entail extra steps for isolation; they are costly; they may involve the formation of potentially toxic compounds such as lysinoalanine, or they may result in the production of chemically derived proteins which are of questionable value for human nutrition.

The nucleic acids (mostly ribosomal ribonucleic acids) in microbial cells exist in the form of tightly bound nucleoprotein complexes. Consideration of the fundamental mechanism of these interactions strongly suggests that hydrophobic forces are the principle forces responsible for the formation of these protein nucleic acid complexes. Thus, destabilization of the hydrophobic interactions between proteins and nucleic acids should facilitate the separation and preparation of microbial proteins and nucleic acids. Because the principal driving force for hydrophobic associations between molecules critically depends upon the structural state of surrounding water molecules, manipulating the structure of water may cause the destabilization of hydrophobic interactions, thereby facilitating separation of the proteins and nucleic acids. Such changes in the structure of water can be induced by chaotropic salts.

DESCRIPTION OF THE INVENTION

The present invention comprises a process for treating nucleoprotein complexes with a chaotropic salt in order to dissociate the nucleic acids from the nucleoprotein complexes, and then isoelectrically precipitating a nucleic acid diminished protein containing fraction from a nucleic acid enriched supernatant. The nucleoprotein complexes for use in the present invention are prepared by disruption of microbial cells.

This invention is broadly applicable to microorganisms; i.e., bacteria, yeasts and fungi, but may also be used with plant, animal and fish cellular materials because the same basic mechanisms occur in these systems. Thus, this method can be appropriately used in research applications and production scale technology as applied to genetic engineering for production of proteinaceous material and nucleic acids. By way of illustration bacteria such as those listed in Table I, yeasts such as those listed in Table II and fungi such as those listed in Table III are suitable microorganisms.

TABLE I—SUITABLE BACTERIA

Acetobacter sp.
Arthrobacter sp.
*Bacillus subtilis*
Corynebacteria sp.
Micrococcus sp.
Pseudomonas sp.

TABLE II—SUITABLE YEASTS

*Candida curvata*
*Candida lipolytica*
*Candida pulcherima*
*Candida utilis*
*Hansenula anomala*

*Hansenula miso*
*Oidium lactis*
*Succharomyces carlsbergensis*
*Saccaromyces fragilis*
*Saccaromyces elipsoideus*
*Trichosporon cutaneum*
*Saccharomyces cerevisiae*
*Candida parapsilosis*
*Hansenula wickerhamii*
*Pichia pastoris*
*Pichia haplophyla*

TABLE III—SUITABLE FUNGI

*Aspergillus niger*
*Aspergillus glaucus*
*Aspergiylus oryzae*
*Aspergillus terreus*
*Aspergillus itaconicus*
*Penicillium notatum*
*Penicillium chrysogenum*
*Penicillium glaucum*
*Penicillium griseofulvum*
*Penicillium funiculosum*
*Fusarium graminearum* (ATCC 20334)
*Fusarium solani* (ATCC 20328)
*Fusarium oxysorium* (ATCC 201281)

For application to food products, yeasts approved by the FDA are the preferred starting materials. Typical starting materials include *Candida utilus, Saccharomyces cerivisiae, Saccharomyces fragilis* and *Saccharomyces carlsbergensis*. However, the present protein recovery process is applicable to all microbial plant and animal cells.

The microbial (animal, fish, plant) cells and/or tissue for the process of this invention can be produced by any conventional method. These microbial cells may be grown aerobically in either a batch or continuous manner. Any suitable carbon-affording substrate may be employed although, for purposes of preparing SCP products for use in foods, an ethanol substrate is preferred. Any conventional combination of mineral nutrient elements may be employed. A convenient source of nitrogen is ammonia which may also be supplied to the fermentor as required to maintain the pH of the fermentation broth, preferably within the range from 3.5 to 5.5. Cells which have been grown at a rapid rate usually have a higher nucleic acid content while those grown more slowly tend to have a more permeable cell wall. Either of these types, as well as cells grown under oxygen-limiting or substrate-limiting conditions may be usefully treated according to the present invention to afford improved and acceptable foods and food components suitable for human consumption.

Rupture of the microbial cells may be accomplished by any suitable physical means at appropriate temperatures. Thus, for example, any homogenizer, colloid mill, ball mill or ultrasonic device may be employed. If a cell wall free or cell wall content reduced protein product is desired, the cell debris can be removed from the aqueous medium by appropriate means, such as centrifugation, preferably after the rupture step. Alternatively, the cell wall content can be retained in the mixture. Typically the disrupted suspension is adjusted to a basic pH preferably ranging from 8 to 9 utilizing aqueous alkali (NaOH). If desired, the cell wall, cell debris and the particulate matter is then removed by filtration or centrifugation. The resultant supernatant containing the nucleoprotein complex is then treated with a chaotropic salt.

Suitable chaotropic salts for use in the present invention include salts employing any effective cation preferably alkali or alkaline earth cations, most preferably sodium or potassium cations. Suitable chaotropic anions for use in the formation of chaotropic salts include but are not limited to the following anions: perchlorate, thiocyanate, trichloroacetate, nitrate, iodide, bromide and urea. The preferred chaotropic salt for food uses is sodium perchlorate, although depending on the end usage of the protein other chaotropic salts can be preferred.

A chaotropic salt is herein defined as a water destructuring agent. Conceptually, the driving force for hydrophobic interaction between two molecules is the unique three-dimensional hydrogen-bonded structure of liquid water. When a chaotropic salt is added, the ion-dipole interaction between the chaotropic ion and water molecules results in breakdown of the unique hydrogen-bonded water structure. Such changes in the bulk water structure weakens the hydrophobic interactions, as discussed in von Hippel, P. H., and Schleich, T. (1969) in *Structure and Stability of Biological Macromolecules* (Timasheff, S. N., and Fasman, G. D., eds.) pp. 417–574, Marcel Dekker, Inc., New York. Since the nucleoprotein complexes are mainly stabilized by hydrophobic interactions, these complexes can be destabilized and dissociated by simply breaking the water structure using a chaotropic salt.

The concentration of the chaotropic anion which is mixed with the nucleoprotein complex (nucleic acid-protein mixture) can vary from 0.1 to 2.0 molality, preferably from 0.3 to 0.7 molality, most preferably from 0.45 to 0.55 molality. These concentrations, particularly in the preferred ranges, produce effective dissociation of the nucleoprotein complex. The amount of chaotropic salt which is employed to produce this effective concentration of chaotropic anions for operation of the protein separation of the present invention is herein defined as an effective nucleoprotein complex dissociating amount. The pH of the nucleoprotein extract from the microbial cell before addition of the chaotropic salt can range from 5 to 10, preferably from about 8 to 9.

The chaotropic salt can be added to the protein-nucleic acid solution either incrementally or continuously. After stirring in the chaotropic salt, the mixture should be stirred intermittently to ensure homogenous interaction. The pH is then adjusted to be acidic, preferably 4.0 to 4.8, most preferably about 4.2 to 4.5 to effect isoelectric precipitation of the proteinaceous material. Typically this acid adjustment is made using hydrochloric or phosphoric acid. The precipitated protein can be recovered by conventional filtration or by centrifugation techniques. The protein precipitate is preferably washed with distilled water at pH 4.2 to remove virtually all traces of the chaotropic salt. The protein precipitate can then be redissolved in water at pH 8-9 and dried for subsequent use. The nucleic acids and chaotropic salt in the supernatant can be separated and recovered by conventional ultrafiltration or precipitation techniques.

The process of the present invention effectively removes over 80% of the nucleic acid initially present in the nucleoprotein. By adjusting the solvent to nucleoprotein ratio, by reextracting, or by a continuous extraction, the nucleic acid levels can be reduced to near zero. Using a single batch extraction, protein preparations containing around 2% nucleic acids can be routinely prepared. By combining different salts more effective reduction of the nucleic acid can be achieved.

Temperature affects the efficiency of nucleic acid reduction. Thus, in the presence of perchlorate a temperature of 25° C. is optimum during the separation phase. However, temperature considerations are independently determined for optimum protein recovery for each individual process.

The process of the invention can be conducted on a continuous or batch basis and can be equally applied to freshly cultured microbial cell materials or to preformed microbial (animal, plant, or fish) proteinaceous materials containing undesirable levels of nucleic acid. All parts and percentages throughout the examples are by weight unless otherwise specified. All temperatures are in degrees centigrade.

A typical embodiment of the invention is described below with reference to the flow chart shown in FIG. 1. *Saccharomyces cerevisiae* or *Saccharomyces carlsbergensis* yeast cells with a nucleic acid content of 12 to 15 grams of nucleic acid per 100 grams of yeast protein are washed with distilled water. A cooled 5 to 10% suspension of these cells in water is homogenized using a Manton Gaulin homogenizer at 8,000 psig (or a Dynomill containing glass beads). Following cell rupture, the cell wall and undisrupted cells together with other particulate matter is removed by filtration or centrifugation at 4° C. All the above operations are conducted at 4° C. The pH is adjusted to 8.5-9 and sodium perchlorate, the chaotropic salt, is added to attain a final chaotropic anion concentration of 0.5 molal. After stirring the salt, the mixture at 15°-27° C. is stirred intermittently. Following complete intermixture of the chaotropic salt with the protein nucleic acid solution, the pH is adjusted to pH of 4.2, using dilute hydrochloric acid in order to isoelectrically precipitate the protein. The precipitated protein is then recovered by filtration or centrifugation. The protein material is washed with distilled water at pH 4.2 and redissolved at pH between 7.5 and 8.5. The protein is then dried and is found to contain less than a two percent content of nucleic acid.

While the invention has been exemplified above, it is understood that other microbial protein containing cellular material such as those described above can be utilized in place of the particular yeast employed. The same is true for the chaotropic salt. Likewise, the process conditions can vary within the skill of the art.

Apart from isolating protein with low nucleic acid content, the process of the invention can also be used for preparing soluble ribonucleic acid from microbial sources thus separating the ribonucleic acid from proteinaceous materials. For this purpose, the supernatant containing nucleic acids and the chaotropic salt can be subjected to diafiltration to remove the salt and nucleotides. The retentate which is enriched in nucleic acids can be further purified by precipitation, ultrafiltration, or via chromatography to remove the protein contaminants. The present invention also can be used for isolation of ribosomal enzymes from microbial sources.

We claim:

1. A method of reducing nucleic acid in microbially derived protein which comprises:
   (a) disrupting microbial cells to provide a mixture comprising protein and nucleic acid,
   (b) mixing the mixture of protein and nucleic acid with an effective nucleoprotein complex dissociating amount of a chaotropic salt, and
   (c) reducing the pH to isoelectrically precipitate a nucleic acid diminished protein concentrate.

2. A method as in claim 1 wherein the protein-nucleic acid mixture is derived from *Candida utilis, Saccharomyces cerevisiae, Saccharomyces fragilis,* or *Saccharomyces carlsbergensis.*

3. A method as in claims 1 or 2 wherein the chaotropic salt is selected from the group consisting of the sodium or potassium salt of perchlorate, thiocyanate, trichloroacetate, nitrate, iodide, bromide or urea.

4. A method of claims 1, 2 or 3 wherein the isoelectric precipitation of the protein concentrate is conducted at a pH of 4.0 to 4.8.

5. In a method of forming a nucleic acid diminished protein concentrate from a mixture of protein and nucleic acid, the steps comprising:
   (a) mixing the mixture of protein and nucleic acid with an effective nucleoprotein complex dissociating amount of a chaotropic salt, and
   (b) reducing the pH to isoelectrically precipitate a nucleic acid diminished protein concentrate.

6. In a method for preparing soluble ribonucleic acids containing reduced amounts of proteinaceous materials, the steps comprising:
   (a) mixing the mixture of protein and nucleic acid with an effective nucleoprotein complex dissociating amount of a chaotropic salt,
   (b) reducing the pH to isoelectrically precipitate a nucleic acid diminished protein concentrate, and
   (c) separating and recovering the ribonucleic acids from the protein concentrate.

* * * * *